United States Patent
Mann Kevehazi

(10) Patent No.: US 11,590,188 B2
(45) Date of Patent: Feb. 28, 2023

(54) COMPOSITION FOR THE TREATMENT OF URINARY TRACT INFECTIONS

(71) Applicant: Laura Mann Kevehazi, Hertfordshire (GB)

(72) Inventor: Laura Mann Kevehazi, Hertfordshire (GB)

( * ) Notice: Subject to any disclaimer, the term of this patent is extended or adjusted under 35 U.S.C. 154(b) by 168 days.

(21) Appl. No.: 17/124,688

(22) Filed: Dec. 17, 2020

(65) Prior Publication Data
US 2021/0187050 A1    Jun. 24, 2021

(51) Int. Cl.
*A61K 36/324* (2006.01)
*A61K 36/9066* (2006.01)
*A61P 13/02* (2006.01)
*A61K 36/82* (2006.01)
*A61K 31/7004* (2006.01)
*A61K 36/67* (2006.01)

(52) U.S. Cl.
CPC ........ *A61K 36/324* (2013.01); *A61K 31/7004* (2013.01); *A61K 36/67* (2013.01); *A61K 36/82* (2013.01); *A61K 36/9066* (2013.01); *A61P 13/02* (2018.01)

(58) Field of Classification Search
CPC .. A61K 36/324; A61K 31/7004; A61K 36/67; A61K 36/82; A61K 36/9066; A61P 13/02
See application file for complete search history.

(56) References Cited

PUBLICATIONS

Huzar, T. (2018). "Can D-mannose treat a UTI?." Medical News Today (323938).
Healthline Medical Network (2019). Can D-Mannose Treat or Prevent UTIs?). https://www.healthline.com/health/d-mannose-for-uti.
Nystul, J. (2017). "Treat A Painful UTI with These Easy Home Remedies." Natural Remedies.
Patel, N., et al. (2014). "Antibacterial Activity of Boswellia Serrata Roxb. Ex Colebr. Ethanomedicinal Plant Against Gram Negative UTI Pathogens." ResearchGate, DOI: 10.1234/lsl.v5310.119.
Perletti, G., et al. (2018). "Resistance of uropathogens to antibacterial agents: Emerging threats, trends and treatments." Archivio Italiano di Urologia e Andrologia (90,2), DOI: 10.4081/aiua.2018.2.85.
Nishimura, M., et al. (2014). "Pumpkin Seed Oil Extracted From Cucurbita maxima Improves Urinary Disorder in Human Overactive Bladder." J Tradit Complement Med. 4(1):72-5, DOI: 10.4103/2225-4110.124355.
Ogunyemi, O. (2018). "Pumpkin Seed Oil For Bladder Health", https://www.stoputiforever.com/interview/pumpkin-seed-bladder/.
Xue, W., et al. (2017). "Intervention effect and mechanism of curcumin in chronic urinary tract infection in rats." Asian Pacific Journal of Tropical Medicine, 10(6): 594-598, http://dx.doi.org/10.1016/j.apjtm.2017.06.009.
Packiavathy, I., et al. (2014). Inhibition of biofilm development of uropathogens by curcumin—An anti-quorum sensing agent from Curcuma longa. ScienceDirect. Food Chemistry, vol. 148 (453-460).
Reygaert, W., et al. (2013). "Green tea as an effective antimicrobial for urintary tract infections caused by *Escherichia coli*." Front Microbiol, 4: 162, DOI: 10.2289/fmicb.2013.00162.
Smith, J. (Copyright 2018) "Green Tea an Adjunct Treatmetn for Urinary Tract Infections". Natural Health Research Institute, Posted 2019. https://protect-us.mimecast.com/s/4va-COYJ1vCxLo9BfDGYLe?domain=naturalhealthresearch.org/.
Thomas, A., et al. (Copyright 2020). ("Isolation and identification of UTI bacteria and inhibition of their growth by some herbal extracts." Research & Reviews in BioSciences, ISSN 0974.7532.
Rath, S., et al. (2014). "Monitoring in vitro antibacterial efficacy of 26 Indian spices against multidrug resistant urinary tract infecting bacteria." ScienceDirect, Integrative Medicine Research, vol. 3, Issue 3 (1331-141). https://www.tsijournals.com/abstract/isolation-and-identification-of-uti-bacteria-and-inhibition-of-their-growth-by-some-herbal-extracts-6648.html.
British Search Report (dated Jun. 26, 2020). Application No. GB1919275.6. filed Dec. 24, 2019.

*Primary Examiner* — Aaron J Kosar
(74) *Attorney, Agent, or Firm* — Howard M. Gitten, Esq.; Lewis Brisbois Bisgaard & Smith LLP

(57) ABSTRACT

A composition for the treatment of UTIs comprising: One of, a monosaccharide L-arabinose, L-frucose, D-mannose, L-rhamnose, L-xylose, lyxose or galactose; Extract from one of *Boswellia serrata, Boswellia sacra* or *Boswellia carteri* containing boswellic acids, terpenes and incensole acetate; Extract from the seeds of one of, Cucurbitaceae *maxima*, Cucurbitaceae *pepo* or Cucurbitaceae *moschata*; Turmeric extract; Green tea extract containing polyphenolic catechins; and, *Piper nigrum*.

14 Claims, No Drawings

COMPOSITION FOR THE TREATMENT OF URINARY TRACT INFECTIONS

CROSS REFERENCE TO RELATED APPLICATIONS

This application claims priority from British Application No. GB2019317.3 filed Dec. 8, 2020, which claims priority of British Application No. GB1919275.6 filed Dec. 24, 2019; the contents and elements of which are herein incorporated by reference for all purposes.

FIELD OF THE INVENTION

The present invention relates to compositions which can be used to treat urinary tract infections. The compositions is antibiotic-free and comprises multiple natural ingredients.

BACKGROUND

Urinary tract infections (UTIs) are generally defined as the presence (>100,000/mL) of bacteria in the urine and symptoms. UTIs are caused by Gram-negative bacteria, particularly *Escherichia coli* (*E-Coli*), in about 90% of reported cases and infect primarily women of all ages This infection is enabled by the adherence and colonization of bacteria to urinary tract epithelial cells. Adherence by *E. coli* is performed by proteinaceous fibres (fimbriae) on the bacteria cell wall, which attach to specific oligosaccharide receptors on uroepithelial cells. Urinary tract infection (UTI) is one of the most frequently seen bacterial infections in primary care and hospital settings patients. In the United States for example, 11% of women over the age of 18 experience one episode of UTI a year. The most common incidences of UTIs occur in women between the ages of 18 to 24 and in the 50+ year old group (this is due in particular to menopause and the decline in oestrogen that makes the epithelium of the urogenital track particularly susceptible to damage and infection). Following the first episode of UTI, the probability of recurrence of a UTI in healthy 18 to 29 year-old women is as high as 24% and 5% of women who have experienced an episode of UTI will suffer multiple episodes within 1 year. The main risk factors identified in women between the ages of 18 to 39 who have suffered with UTIs are sexual relationship and a history of recurrent UTI.

Recurrent UTI is defined as three episodes with the last twelve months or two episodes in the last six months.

The treatment for UTIs involves the use of antibiotics, this however causes antibiotic resistance among uropathogenic microorganisms and disturbs the healthy balance of the intestinal microbiota. Repeated use of antibiotics in the treatment of women who suffer recurrent UTIs has significantly contributed to multiple strains of antibiotic resistant bacteria, resulting in serious chronic infections extremely difficult to control.

Antibiotic-free protective approaches to managing UTIs have gained popularity in recent years worldwide, particularly in managing recurrent UTIs. This gain in popularity is to do with the growing resistance to multiple classes of antibiotics and the urgent need for antibiotic-free treatment alternatives, as well as the absence of side effects, like for example: yeast infections, liver and kidney damage as well as disruption of the normal intestinal flora responsible for the human immune response.

It is an object of the current invention to provide an antibiotic free composition that can both provide symptom relief as well as comprehensively address the etiology of UTIs, on several levels: antibacterial, anti-inflammatory as well as calming the overactive bladder, which does not create bacterial resistance or serious disturbances to the intestinal flora.

Statement of Invention

A first aspect of the present invention provides a composition comprising:
D-mannose;
Extract from one of *Boswellia serrata, Boswellia sacra* or *Boswellia carteri* containing boswellic acids, terpenes and incensole acetate;
Pumpkin seed extract;
Turmeric extract;
Green tea extract containing polyphenolic catechins; and
*Piper nigrum.*

A second aspect of the present invention provides a composition comprising:
D-mannose from 400 mg-500 mg per single dose;
Extract from one of *Boswellia serrata, Boswellia sacra* or *Boswellia carteri* containing boswellic acids, terpenes and incensole acetate from 100-200 mg per single dose;
Pumpkin seed extract from 100-200 mg per single dose;
Turmeric extract from 100 mg per single dose;
Green tea extract containing polyphenolic catechins from 30 mg per single dose; and,
*Piper nigrum* from 5 mg per single dose.

A third aspect of the present invention provides a composition in the form of a powder comprising:
D-mannose in an amount from 400-500 mg per single dose;
*Boswellia* extract having at least 65% boswellic acid, from 100-200 mg per single dose;
Water soluble pumpkin seed extract from 100-200 mg per single dose;
Turmeric extract containing 65-95% curcuminoids, from 100-200 mg per single dose;
Green tea EGCG extract, from 30-50 mg per single dose; and,
*Piper nigrum* from 5-10 mg per single dose.

A fourth aspect of the present invention provides a composition in the form of a liquid or gel comprising:
D-mannose in an amount from 400-500 mg per single dose;
*Boswellia* extract having at least 65% boswellic acid, from 100-200 mg per single dose;
Pumpkin seed oil extract from 100-200 mg per single dose;
Turmeric extract containing 65-95% curcuminoids, from 100-200 mg per single dose;
Green tea EGCG extract, from 30-50 mg per single dose; and,
*Piper nigrum* from 5-10 mg per single dose.

A fifth aspect of the present invention provides a composition in the form of a liquid or gel comprising:
D-mannose in an amount from 1500-1700 mg per single dose;
*Boswellia* extract having at least 65% boswellic acid, from 300-500 mg per single dose;
Pumpkin seed oil extract, from 500-700 mg per single dose;
Turmeric extract containing 65-95% curcuminoids, from 500-700 mg per single dose;
Green tea EGCG extract, from 90-150 mg per single dose; and,
*Piper nigrum* from 5-20 mg per single dose.

A sixth aspect of the present invention provides a composition in the form of a power in a capsule comprising:
  D-mannose 400 mg,
  Pumpkin seed extract equivalent to 150 mg,
  Turmeric extract equivalent to 150 mg,
  *Boswellia Serrata* extract equivalent to 100 mg,
  Green Tea Extract 95% Polyphenols 30 mg,
  Black pepper 5 mg; and optionally a pharmaceutically acceptable carrier, excipient or diluent.

The pumpkin seed extract is preferably from the seeds of one of Cucurbitaceae *maxima*, Cucurbitaceae *pepo* or Cucurbitaceae *moschata*.

The compositions in the form of a liquid or a gel can be in a suitable vehicle such as PEG, or coconut oil and added flavourings and natural sweeteners like stevia.

The compositions described herein may consist of the above listed ingredients and optionally also including a pharmaceutically acceptable carrier, excipient or diluent.

A further aspect of the present invention is the composition for use in combating and reliving the symptoms of a urinary tract infection, the composition for use in for combating the recurrence of a urinary tract infection or for use as an antispasmodic for those suffering with overactive bladder syndrome.

The compositions of the present invention may be used as a medicament.

The composition may be used for combating and reliving the symptoms of a urinary tract infection.

The composition may be used for combating the recurrence of a urinary tract infection.

The composition may be for used as an anti-spasmodic for those suffering with overactive bladder syndrome.

The composition may be used for combating post coital/sexual activity triggered UTIs.

The composition may be used in the treatment of a urinary tract infection by administering four capsules three times a day for a minimum of 5 days, wherein the capsule comprises:
  D-mannose 400 mg,
  Pumpkin seed extract 10:1 (equivalent to 150 mg),
  Turmeric extract 10:1 (equivalent to 150 mg),
  *Boswellia Serrata* extract 5:1 (equivalent to 100 mg),
  Green Tea Extract 95% Polyphenols 30 mg,
  Black pepper 5 mg; and optionally a pharmaceutically acceptable carrier, excipient or diluent.

DETAILED DESCRIPTION OF THE INVENTION

Aspects and embodiments of the present invention will now be discussed. Further aspects and embodiments will be apparent to those skilled in the art.

Due to antibiotics overuse over the last decades both in industrial farming and human medicine, today in the UK, close to half of bacterial infections do not respond to the main classes of antibiotics. Many cases of UTIs tend to complicate, affect the kidneys requiring hospitalization and treatment with intravenous antibiotics. In addition, over 20%-30% of Sepsis cases originate in the urinary tract.

Therefore, the search for novel strategies is even more important as microbial biofilms offer resistance to conventional antibiotics, antiseptics and disinfectants, and are involved in the frequent treatment failures of some chronic inflammatory diseases and wounds.

Exclusive focus on individual biochemical effect neglects the fact that multiple constituents may prove more potent and effective than a single compound or that interactions of co-occurring phytochemicals may help nullify side effects of individual components.

The claimed compositions target the bacterial colonisation of the bladder, through several combined mechanisms. The specific combination of ingredients target the bacterial colonisation of the bladder, through several combined mechanisms including the disruption of the biofilm and an attachment type antibacterial mechanism.

The (physical) attachment type antibacterial mechanism is superior to antibiotics because it does not cause antibiotic resistance permitting long term administration without inducing antibiotic resistance. It also does not interfere with/disrupt the host cellular biochemistry. In addition, antibiotics and antiseptics cannot penetrate the mucus like biofilm layer and it is extremely difficult to treat chronic biofilm infections with the standard medical treatments, making them a serious health threat.

D-mannose works by attracting the bacterial fimbriae in the bladder which then attaches to the D-mannose. D-mannose with the attached bacterial fimbriae is excreted with the urine reducing the bacterial load in the urinary tract. This is an attachment/physical type antibacterial mechanism.

D-mannose alone for treating urinary tract infections is known. However, D-mannose alone is not effective in cases of established/chronic infections characterised by the biofilm presence, as it cannot disrupt or penetrate the biofilm polymeric layer and can only bind with free floating, planktonic bacteria present in urine through the physical attachment mechanism. Therefore, there is a need to disrupt or penetrate the biofilm so that D-mannose can then attach to the bacterial fimbriae of the Urinary pathogen *E. coli* in the bladder and simply eliminate it with the urine when the bladder is emptied Turmeric, *Boswellia* and the Green Tea extracts have the ability to prevent, disrupt and penetrate biofilm formation. This confers the preventive effect of the current composition. Taken at the first symptoms it swiftly deals with the bacterial bladder colonization, stopping the bacteria from settling in the bladder and causing chronic, difficult to treat infections. Equally, taken when the biofilm was already formed, the disruptive and penetrating effect then allows the D-mannose to then reach and remove the bacteria under the biofilm. This provides an extremely effective composition.

The Quorum sensing activity of Turmeric component Curcumin, directly inhibits the biofilm formation by uropathogens.

*Piper nigrum* enhances the absorption and activity of Turmeric extracts.

The claimed composition targets the bacterial colonization of the bladder, the inflammatory damage of the urinary epithelium and the overactive bladder symptoms through several combined mechanisms as follows:

The antibacterial activity against both Gram negative and Gram positive bacteria, both through physical attachment and elimination with urine voiding (D-mannose) as well as direct damage of the bacterial cellular wall (Turmeric, *Boswellia*, Green tea), which achieves better results than the main antibiotics used to treat UTI.

Inhibition and Disruption of biofilm (Turmeric, *Boswellia*, Green Tea extracts) composition prevents bacterial settlement in the Urothelium and the inherent chronic infection caused by biofilm development. Disruption of existing biofilm enables exposure of bacterial colonies previously protected by the polymeric extracellular layer, exposing them to the combined antibacterial activity of all the ingredients.

Enhanced Host Immune response—the biofilm layer prevents the normal signaling by which the pathogens trigger the host immune system. The immune system cannot fight the bacteria protected by the biofilm layer, but the disruption of the biofilm automatically triggers the macrophages attack of the bacterial cells.

Combined anti-inflammatory mechanisms: as a potent immunomodulatory agent in T cells, B cells, neutrophils, natural killer cells, dendritic cells, and macrophages Turmeric leads to the suppression of TNF-α release, enhance and modulate the immune response to severe inflammation. Boswellic acids inhibit the pro-inflammatory modulators—leukotrieme, increase vascular permeability, and reduce the glycosaminoglycans degradation thus protecting the mucosal tissues of the urinary tract.

Green Tea and its main polyphenol EGCG suppress the gene and/or protein expression of inflammatory cytokines and inflammation-related enzymes.

Unlike antibiotics, these ingredients are active at concentrations that do not interfere with bacterial growth or survival but inhibit the formation of bacterial biofilms or disrupt already existing biofilms by targeting biofilm-related structures or regulation. Thereby, they can act synergistically with antibiotics and/or allow the immune system to attack bacteria that would otherwise be hidden away in biofilms.

Another beneficial aspect of the current composition is that D-mannose is used in total daily amounts of up to 5-6 grams. This is enabled by the combination with the other ingredients, thus avoiding the unpleasant side effects of higher D-mannose doses. Used as a single ingredient, in order to be effective, D-mannose needs to be taken in doses of 15-24 grams/day, which is known to cause highly unpleasant side effects bloating, gas and diarrhea, deterring patients already suffering from UTIs from completing the treatment.

Therefore, each component of the composition works together with different mechanisms in order to provide extremely effective composition for treating urinary tract infections. An unexpected effect of the claimed composition therefore is the biofilm disruption and eradication which exposes the previously hidden bacterial colonies, enabling the host immune mechanisms to recognised the pathogens and target them.

The combination of the specific ingredients of the invention provides an extremely effective treatment for UTI infections by using multiple combined different mechanisms. It is demonstrated in the examples that all of the symptoms of UTI infections are alleviated when the claimed composition is administered which shows the combination of ingredients and multiple mechanisms is extremely effective.

The symptoms of UTIs can include: dysuria, lower abdominal pain/pressure, urgency to urinate, frequent urination, cloudy urine (due to high number of leukocytes), or haematuria (blood in urine), all negatively impacting the wellbeing and the ability to work and travel. The claimed compositions have been shown to effectively alleviate all of these symptoms in different patients. Therefore, the claimed composition and the specific combination of ingredients have been shown to be extremely effective in treating urinary tract infections and their reoccurrence than could have been expected from the prior art.

An additional unexpected effect of the claimed composition is the absence of dysmenorrhea (otherwise known as "menstrual cramps") in women during the time they took the composition for UTI. The women aged 30-41 previously suffered severe abdominal cramping in the first days of their menstrual cycle, needing Ibuprofen/Paracetamol for pain management. During the 12 weeks when they received the herbal composition, they reported no dysmenorrhea during their menstrual period. Therefore, the claimed composition is extremely effective in the treatment of UTI's as well as dysmenorrhea.

A further unexpected effect of the composition is the statistically significant reduction of the number and severity of the hot flashes experienced by women over 50 taking the herbal composition.

Therefore, as well as being effective for the treatment of UTI's the claimed composition improves the wellbeing of the patient by the unexpected effects of significantly reducing the number and severity of hot flashes experienced by women over 50 and eradicating dysmenorrhea for women ages 30-41.

Composition of the Invention

There are currently no single compositions available that address the etiology and all symptoms of both acute, chronic, interstitial cystitis as well as preventing recurrence UTIs, without the use of antibiotics which create bacterial resistance and serious disturbances of the intestinal flora.

A preferred composition would include:
1) One of; a monosaccharide L-arabinose, L-fucose, D-mannose, Lrhamnose, L-xylose, lyxose or galactose;
2) Resinuos extracts derived from trees of genus *BOSWELLIA* part of BURSERACERA plant family, including *Boswellia serrata, Boswellia sacra* and *Boswellia carteri* containing extracts of Boswellic acids, terpenes and incensole acetate;
3) Extract from seeds of Curcubitacea family: *maxima, pepo* and *moschata*. For example, pumpkin which is an edible fruit found in the American and European continents and is grown in Asia and Africa;
4) Turmeric, extracts from the roots of *Curcuma longa* L. and *Curcuma sinensis* belonging to the Zingberacea family;
5) Green tea extract containing polyphenolic catechins; and,
6) Black Pepper/*Piper nigrum*.

A preferred monosaccharide is D-mannose.

Another preferred composition consists of:
1) D-mannose;
2) Resinuos extracts derived from trees of genus *BOSWELLIA* part of BURSERACERA plant family, including *Boswellia serrata, Boswellia sacra* and *Boswellia carteri* containing extracts of Boswellic acids, terpenes and incensole acetate;
3) Pumpkin seed extract;
4) Turmeric, extracts;
5) Green tea extract containing polyphenolic catechins; and,
6) Black Pepper/*Piper nigrum*.

These preferred compositions may optionally also include a pharmaceutically acceptable carrier or excipient. These preferred compositions may consist only of the ingredients listed above and optionally also include a pharmaceutically acceptable carrier or excipient.

Each of these components and their benefits are discussed below.
1) One of; a monosaccharide L-arabinose, L-fucose, D-mannose, Lrhamnose, L-xylose, lyxose or galactose.

D-mannose is metabolized in negligible amounts by humans, and swiftly eliminated through the urinary tract. When present in urine it attracts the bacterial fimbriae to attach to the D-mannose, thus preventing Gram-negative bacterial epithelial adherence, and the creation of the dreaded biofilm leading to chronic infections that are very challenging to treat. The linkage results into elimination of bacteria from the body.

D-mannose works by physical attachment to the *E. coli* present in urine. D-mannose offers an alternative binding site to the *E. coli* that has a high affinity to attach to the epithelial cells of the Urothelium, via a Mannose-binding lectin, FimH located at the tip of the bacterial pillus. D-mannose with the attached *E. coli* is excreted with the urine reducing the bacterial load in the urinary tract without any adverse impact on the structure urinary epithelium. This attachment type antibacterial mechanism is superior to antibiotics because it does not cause antibiotic resistance permitting long term administration without inducing antibiotic resistance.

2) Resinuos extracts derived from trees of genus BOSWELLIA part of BURSERACERA plant family, including *Boswellia serrata, Boswellia sacra* and *Boswellia carteri* containing extracts of Boswellic acids, terpenes and incensole acetate.

The noted effects are anti-inflammatory in both acute and chronic cases through cytokine inhibition, enhanced healing of the affected tissues, reduced swelling and cancer protection effect.

3) Extract from seeds of Curcubitacea family: *maxima, pepo* and *moschata*. For example, pumpkin which is an edible fruit found in the American and European continents and is grown in Asia and Africa.

The extract of the seed is a rich source of vitamins, linoleic acid, oleic acid, and microelements. It has been proven as useful for the treatment of urinary disorders, specifically acting as antispasmodic, and significantly improving symptoms of OAB (overactive bladder).

4) Turmeric, extracts from the roots of *Curcuma longa* L. and *Curcuma sinensis* belonging to the Zingberacea family.

Turmeric needs very little introduction, it has been used for millennia treating various inflammatory conditions. Its anti-inflammatory effect is exerted by modulation of cytokines, downregulation of NF-kB (a pro-inflammatory pathway) and the inhibition of cydooxygenase enzymes. Turmeric extract is better absorbed in presence of Pepper nigrum.

5) Green tea extract: the major beneficial components of green tea have been characterized, and are now known to be polyphenolic catechins. The main catechins in green tea are (−)-epicatechin-3-gallate, (−)-epigallocatechin (EGC), (−)-epicatechin, and (−)-epigallocatechin-3-gallate (EGCG). EGCG and EGC have been shown to have the greatest antimicrobial effect.

The highest antimicrobial activity of tea is due to presence of catechins and polyphenols which damage the bacterial cell membrane. There are multiple, different mechanisms for antimicrobial effects of green tea such as: Catechins induce production of cytokines such as IL-10 and IL-12. Catechin-copper (II) complexes damage the cytoplasmic membrane of *E. coli* and by blocking the connection of conjugated R plasmid in *E. coli*, have bactericidal and antitoxin effects. Green tea polyphenols decrease tumour necrosis factor-(X gene expression, which is important in pathogenesis of *E. coli* infection. EGC can bind to the ATP site of the DNA gyrase β subunit of bacteria and inhibit the activity of the gyrase enzyme.

6) Black Pepper/*Piper nigrum*.

*Piper nigrum* enhances the absorption and activity of Turmeric extracts.

The proposed composition is a novel formulation consisting of multi-functional substances backed by extensive research that enables a unique synergistic and comprehensive effect.

It addresses symptoms of bladder pain, burning sensation, frequent urination, over active bladder symptom OAB and helps prevent recurrent UTI's.

It provides an anti-bacterial, anti-inflammatory, antispasmodic activity while simultaneously exercising a healing action on the urothelium (epithelium lining of the urinary track) prevents bacterial re-adherence and recolonization and improves overactive bladder symptoms.

Multi-functional herbal components as formulated in this novel composition exert a synergetic effect when used together. The strong synergy of multiple constituents offers a far superior effect to existing preparations (prior art) that cannot be obtained with using single compounds.

Turmeric, *Boswellia* and Green Tea, exhibit complex antibacterial activity by targeting and damaging the bacterial cellular wall as well as a healing and strengthening of the mucosal tissues. The antibacterial activity is not limited antibiotic sensitive bacteria, it negatively interacts with all existing bacteria, importantly, with the antibiotic resistant species that do not respond to antibiotic treatment or require maximum dosage of combined antibiotics. The high doses of antibiotics are resulting serious side effects (examples: Fluoroquinolones damage the nervous system and cause spontaneous tendons tears, Nitrofurantoin can cause kidney damage and in larger doses can lead to organ failure).

The combination of Curcumin and *Boswellia* provides a powerful anti-inflammatory effect. Curcumin can significantly improve the symptoms of chronic urinary tract infections, protect renal tubular function, and also decline inflammatory responses by influencing the expressions of TLR2 mRNA and TLR4 mRNA so as to exert its curative effect on chronic urinary tract infections. Boswellic acids exhibit potent anti-inflammatory properties in vitro and in vivo. Therefore, the combination of these ingredients along with the other components of the invention provide an anti-inflammatory effect.

Due to all the effects discussed the present composition reduces the need for antibiotic treatment, reduces the risk of antibiotic resistance and prevents destruction of healthy gut micro biota due to frequent antibiotic treatments.

Biofilm Disruption

About 80% of human infections affecting the gastrointestinal, genitourinary and respiratory systems, oral mucosa and teeth, eyes, middle ear and skin are caused by biofilm-associated microorganisms.

The number of chronic, difficult to treat infections has skyrocketed in the last decade, they are very difficult to eradicate, and extremely challenging for the medical professionals and patients alike. Although starting as simple infections, very quickly the pathogens attach themselves to the tissues, start forming colonies, and start secreting a mucus type substance called extracellular polymers that is hosting the bacteria.

Most bacteria form biofilms, which are multicellular microbial communities embedded in a self-produced exopolymeric substance (EPS) largely composed of a protein anchor and different extracellular polymers. Bacteria within a mature biofilm community exist in an altered metabolic state and different physical environment than their free-floating, or planktonic, relatives. Biofilm bacteria generally tolerate antibiotic treatment, and antibiotics can induce biofilm formation.

The effect of the proposed composition exposes bacteria in the biofilm to the antibacterial activity of the ingredients that enables targeting of Gram negative bacteria by the different ingredients.

Biofilms are very complex and powerful environments with multiple functions:
- act as an invisibility shield, helping bacteria hide to avoid detection and destruction by the immune system
- form a physical barrier protecting the bacteria from antimicrobial agents like antibiotics
- allow bacteria to freely exchange genetic material and mutate
- make any laboratory testing to isolate the responsible bacteria extremely difficult Biofilms develop equally on living and non-living surfaces, for example the slippery layer on stones at water edge, slimy layers on kitchen surfaces, and the dental plaque accumulating on our teeth few hours after dental brushing.

Biofilms are responsible for accelerating the process of antimicrobial resistance that renders the main classes of antibiotics useless.

Antibiotics and antiseptics cannot penetrate the mucus like biofilm layer and with the standard medical treatments it is extremely difficult to treat chronic biofilm infections, making them a serious health threat.

While mechanical removal is suitable in the oral cavity, in chronic wounds, or removing a biofilm infected catheter, the majority of the human infections cannot be resolved in a similar fashion.

D-mannose alone is not effective in cases of established/chronic infections characterised by the biofilm presence, as it cannot disrupt or penetrate the biofilm polymeric layer and can only bind with free floating, planktonic bacteria present in urine through the physical attachment mechanism. However this can be achieved with the other components of the composition because Turmeric, *Boswellia* and the Green Tea extracts have the ability to disrupt biofilm formation, penetrate biofilms and exert antibacterial activity superior to antibiotics and without side effects. Disruption of the biofilm by Quorum sensing activity of Curcumin also leads to inhibition of biofilm development of uropathogens. The active ingredients in *Boswellia seratta* extract are Boswellic Acids (BA) these have been found to effectively inhibit the formation as well as eradicating the preformed biofilms of *S. aureus* and *S. epidermidis* biofilms. The Green Tea Polyphenol Epigallocatechin-3-gallate) EGCG prevents the formation of amyloid curli fibres and pEtN-cellulose; i.e., the two major components of the extracellular matrix of macro colony biofilms of *E. coli*.

Unlike antibiotics, these ingredients are active at concentrations that do not interfere with bacterial growth or survival but inhibit the formation of bacterial biofilms or disrupt already existing biofilms by targeting biofilm-related structures or regulation. Thereby, they can act synergistically with antibiotics and/or allow the immune system to attack bacteria that would otherwise be hidden away in biofilms.

The result of the biofilm disruption exposes bacteria in the biofilm to the antibacterial activity of the ingredients that enables targeting of Gram negative bacteria by the D-mannose through the attachment mechanism, as well as direct targeting of both Gram negative and Gram positive bacteria by Turmeric, *Boswellia* and Green Tea extracts through cellular wall destruction.

Therefore an unexpected effect of the claimed composition is the biofilm disruption and eradication this exposes the previously hidden bacterial colonies, enabling the host immune mechanisms to recognise the pathogens and target them.

In addition, because of the disruption to the biofilm the claimed composition can be administered with together with antibiotics. This can improve the efficacy of the antibiotics by allowing access to the biofilm.

Reduction in Side Effects

Another beneficial aspect of the current composition is that D-mannose is used in total daily amounts of up to 5-6 grams. This is enabled by the combination with the other ingredients, thus avoiding the unpleasant side effects of higher D-mannose doses. Used as a single ingredient, in order to be effective, D-mannose needs to be taken in doses of 15-24 grams/day, which is known to cause highly unpleasant side effects bloating, gas and diarrhea, deterring patients already suffering from UTIs from completing the treatment. The proposed composition, through the combined effects of the ingredients, avoids the need to use the quantities of D-mannose which has the advantage of avoiding side effects.

Yeast infections are recognised as common side effects of antibiotic treatments, using the claimed composition prevents such an outcome, thus preventing additional complications of antibiotics.

Dose

The composition could take the form of a powder, liquid or gel and can be used for the purpose of relieving and combating symptoms of UTI by administering the composition to help clear *E. coli* urinary tract infections—representing 90% of cases, where the composition is administered in the form of capsules, tablets, powder or gel by taking 3 capsules three times a day for 3 days followed by 2 capsules twice daily for 10 days. The composition can be administered in the form of capsules, tablets, powder or gel by taking 4 capsules three times a day for 5 days followed by 2 capsules twice daily for 10 days. The composition can be administered in the form of capsules three times a day (12 capsules a day) for 5 days followed by two capsules twice a day for 3 months (12 weeks). Each capsule contains the excipients listed below.

The composition can be administered as a powder in a capsule, wherein the capsule is a vegetarian capsule of HydroxypropylMethylCellulose. The composition can also be administered in the form of a gel in a sachet, the gel embodiment can include Phosphatidylcholine (Soy Lecithin), Flavouring, Natural sweetener (stevia) and Potassium Sorbate preservative.

In a preferred embodiment the capsules comprise:
D-mannose;
Extract from one of *Boswellia serrata, Boswellia sacra* or *Boswellia carteri* containing boswellic acids, terpenes and incensole acetate;
Pumpkin seed extract;
Turmeric extract;
Green tea extract containing polyphenolic catechins;
*Piper nigrum*; and optionally
a pharmaceutically acceptable carrier, excipient or diluent.

In another preferred embodiment the capsules comprise:
D-mannose 400 mg,
Pumpkin seed extract 10:1 (equivalent to 150 mg),
Turmeric extract 10:1 (equivalent to 150 mg),
*Boswellia Serrata* extract 5:1 (equivalent to 100 mg),
Green Tea Extract 95% Polyphenols 30 mg,
Black pepper 5 mg and optionally a pharmaceutically acceptable carrier, excipient or diluent.

In another preferred embodiment the gel in a sachet comprises or consists of the components listed above and optionally includes Phosphatidylcholine (Soy Lecithin), Flavouring, Natural sweetener (stevia) and Potassium Sorbate preservative. The gel sachet can include multiple doses of the capsule.

Preferred compositions described herein may consist of D-mannose, Extract from one of *Boswellia serrata*, *Boswellia sacra* or *Boswellia carteri* containing boswellic acids, terpenes and incensole acetate, Pumpkin seed extract, Turmeric extract, Green tea extract containing polyphenolic catechins, *Piper nigrum*; and optionally a pharmaceutically acceptable carrier, excipient or diluent.

Use

The composition can also be used to help prevent UTI's as well as the recurrence of UTI's.

The composition may also be used for helping to heal the chronic condition of Interstitial Cystitis through the synergetic effect of the phytochemicals present in the composition by administering 2 capsules twice daily for 24 weeks.

The composition also has the beneficial effect of exerting an anti-spasmodic effect beneficial in patients suffering from OAB (overactive bladder syndrome).

The composition may also be used for preventing re-infection following sexual activity by administering the composition in the form of 2 capsules 1 hour before sexual activity and 2 capsules after activity, followed by taking 2 capsules twice the next day. The composition may also be administered in the form of a single dose (4 capsules, or 1 sachet) 1 hour before sexual activity and another dose (4 capsules or 1 sachet) after activity, followed by taking 2 capsules twice the next day.

Preferred capsules with their preferred excipients and amounts is listed above.

The invention has been described with reference to a preferred embodiment. The description is intended to enable the skilled person to make the invention, not to limit the scope of the invention. The scope of the invention is determined by the claims.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

Example 1

Subjects and context:

Eight subjects (female, ages 30 32, 38, 41, 55, 56, 59, 60) with recurrent monthly UTI symptoms were treated according to an embodiment of the invention.

Prior to the treatment, the mid-stream urine (MSU) was collected in sterile containers and tested using test strips common in the art for the analysis of urinary tract infection (MULTISTIX GP, Siemens), following the instructions from the manufacturer. All the tests indicated presence of UTI.

Treatment procedure:

Treatment proceeded in two phases, the first lasting five days, and the second for a further three months. Urine was collected and tested for urinary tract infection at the end of the first phase.

Symptoms were recorded in a self-assessment questionnaire on the first day, at the end of the first week and at the end of the three months period. The symptoms of the patients were recorded by answering/reporting the following criteria:

1. Dysuria (pain when passing urine),
2. Lower abdominal pressure/pain,
3. Urgency to urinate,
4. Frequency of urination during the day,
5. Aspect of urine (clarity, colour and smell).
6. General wellbeing Administration composition:

D-mannose 400 mg,

Pumpkin seed extract 10:1 (equivalent to 150 mg),

Turmeric extract 10:1 (equivalent to 150 mg),

*Boswellia Serrata* extract 5:1 (equivalent to 100 mg),

Green Tea Extract 95% Polyphenols 30 mg,

Black pepper 5 mg.

This composition was administered orally in hydroxypropylmethylcellulose capsules.

Administration protocol:

For the first phase, four capsules were taken three times a day with food and water (12 capsules a day) for 5 days.

For the second phase, two capsules were taken twice a day for 3 months (12 weeks).

Results:

After completing 5 days of treatment, the MSU was collected and tested as described above. All eight results showed no sign of urinary tract infection.

After one week the participants reported resolution of symptoms as follows:

Dysuria and the lower abdominal pressure were cleared after 5 days, the frequency of urination was reduced from 1-2 times an hour as recorded at the start, to once every 2-3 even 4 hours.

The painful urgency to urinate was not present at day six. Aspect of urine (colour, clarity, smell) became normal after the first week.

At the end of the three month period, there were no reports of recurring dysuria or abdominal pain symptoms with urination frequency reported as normal and no painful urgency present. Urine aspect was reported as normal.

Additionally, a statistically significant reduction in the number and intensity of hot flashes for the women over 50 age group by 80±5%, with increased energy levels was observed at the end of the three month period.

The women in the 30-41 age group reported absence of dysmenorrhea ("menstrual cramps") previously occurring at day 1-2 of their monthly menstrual cycle that required pain management with ibuprofen/paracetamol in the past.

This is indicative of a novel synergy between the constituents in this composition and shows a potent beneficial effect to some of the most susceptible victims of UTI; menopausal and post-menopausal women.

Example 2

Subjects and context:
Two subjects suffering from Type 2 diabetes mellitus (female, 60 and male, 64) reporting recurrent UTIs were treated according to an embodiment of this invention.

Prior to the treatment, urine samples were tested as in Example 1. Both samples showed the presence of leucocytes, nitrites and erythrocytes, indicating a UTI.

Treatment procedure:
Treatment progressed in two phases. The first lasted seven days, and the second continued for a further six months. Urine was tested at three instances: the end of the first phase, 12 weeks into the study, and at the end of the second phase. Symptoms were additionally recorded in the aforementioned self-assessment questionnaire from Example 1.

Administration composition:
D-mannose 400 mg,
Pumpkin seed extract 10:1 (equivalent to 150 mg),
Turmeric extract 10:1 (equivalent to 150 mg),
*Boswellia Serrata* extract 5:1 (equivalent to 100 mg),
Green Tea Extract 95% Polyphenols 30 mg,
Black pepper 5 mg.

This composition was administered orally in hydroxypropylmethylcellulose capsules.

Administration Protocol:
For the first phase, four capsules were taken three times a day with food and water (12 capsules a day).

For the second phase, two capsules were taken twice a day.

Results:
After the first phase, both subjects reported marked improvement in terms of dysuria, frequency and urgency of urination with visibly clearer urine. Urine testing showed only a minimal presence of leucocytes, a marked improvement from the initial test.

During the second phase, the self-assessment of symptoms demonstrated that both subjects remained symptom free.

At 12 weeks, neither subjects' urine samples showed any indication of UTI. At the end of the second phase, the urine samples remained absent of UTI indicators and no UTI symptoms were reported.

This can be compared to the subjects' situation before the study. Each had previously taken antibiotics to ameliorate their UTI symptoms—6-9 months of Cephalexin 500 mg twice daily—but had experienced the unpleasant, yet common, side effects of nausea, diarrhoea and yeast infections (oral and vaginal), with the added issue that the UTI symptoms had reoccurred after the course of antibiotics was completed.

This example demonstrates both the effectiveness compared to regular antibiotic treatments prescribed in response to many UTIs, and the completely different nature of a treatment which can be administered over the long-term without concern for physiological side effects or the development of drug resistance. Particularly, the composition has a preventive effect as it can be administered concurrently with other treatments and also long term to patients with chronic conditions/co-morbidities preventing additional complications occurring in such cases such as kidney damage or serious infections.

Example 3

Subjects and context:
A subject (female, 45) reporting consistent UTI symptoms triggered by sexual activity was treated according to an embodiment of this invention.

Reported symptoms before the commencement of treatment were dysuria and urgency to urinate every 30 minutes. Previously the subject had reported that alleviation of her symptoms was possible by sexual abstinence, or by taking an antibiotic (nitrofurantoin) after sexual activity.

Administration composition:
D-mannose 1600 mg,
Pumpkin seed extract 10:1 (equivalent to 600 mg),
Turmeric extract 10:1 (equivalent to 600 mg),
*Boswellia Serrata* extract 5:1 (equivalent to 400 mg),
Green Tea Extract 95% Polyphenols 120 mg,
Black pepper 20 mg.

This composition was administered orally in the form of a gel sachet consisting additionally of soy lecithin (phosphatidylcholine), flavouring, sweetener-stevia and potassium sorbate preservative.

Administration protocol:
One sachet was taken one hour before sexual activity. A further sachet was taken immediately following sexual activity, and a final sachet the following day.

Results:
The subject reported that following the first dose no post coital symptoms occurred. The subject continued treatment thereafter, and reported no further instances of UTI following six months of using the gel composition.

The immediate resolution of symptoms is a surprising result which indicates the powerful efficacy of this composition in preventing bacterial adherence and colonisation of the bladder and the protective/preventive effect on the urinary epithelium.

The invention claimed is:
1. A composition comprising effective amounts of:
    D-mannose;
    extract from one of *Boswellia serrata, Boswellia sacra*, or *Boswellia carteri* containing boswellic acids, terpenes, and incensole acetate;
    pumpkin seed extract;
    turmeric extract;
    green tea extract containing polyphenolic catechins; and
    *Piper nigrum*.

2. The composition according to claim 1, comprising:
D-mannose from 400 mg-500 mg per single dose;
extract from one of *Boswellia serrata, Boswellia sacra*, or *Boswellia carteri* containing boswellic acids, terpenes, and incensole acetate from 100-200 mg per single dose;
pumpkin seed extract from 100-200 mg per single dose;
turmeric extract from 100 mg per single dose;
green tea extract containing polyphenolic catechins from 30 mg per single dose; and, *Piper nigrum* from 5 mg per single dose.

3. The composition according to claim 2, in the form of a powder comprising:
D-mannose in an amount from 400-500 mg per single dose;
from 100-200 mg per single dose *Boswellia* extract having at least 65% boswellic acid;
water soluble pumpkin seed extract from 100-200 mg per single dose;
from 100-200 mg per single dose turmeric extract containing 65-95% curcuminoids;
green tea EGCG extract, from 30-50 mg per single dose; and,
*Piper nigrum* from 5-10 mg per single dose.

4. The composition according to claim 2, in the form of a liquid or gel, comprising:
D-mannose in an amount from 400-500 mg per single dose;
from 100-200 mg per single dose *Boswellia* extract having at least 65% boswellic acid;
pumpkin seed oil extract from 100-200 mg per single dose;
from 100-200 mg per single dose turmeric extract containing 65-95% curcuminoids;
green tea EGCG extract, from 30-50 mg per single dose; and,
*Piper nigrum* from 5-10 mg per single dose.

5. The composition according to claim 1, in the form of a powder, comprising:
D-mannose in an amount from 400-500 mg per single dose;
from 100-200 mg per single dose *Boswellia* extract having at least 65% boswellic acid;
water soluble pumpkin seed extract from 100-200 mg per single dose;
from 100-200 mg per single dose turmeric extract containing 65-95% curcuminoids;
green tea (−)-epigallocatechin-3-gallate (EGCG) extract from 30-50 mg per single dose; and,
*Piper nigrum* from 5-10 mg per single dose.

6. The composition according to claim 1, in the form of a liquid or gel, comprising:
D-mannose in an amount from 400-500 mg per single dose;
from 100-200 mg per single dose *Boswellia* extract having at least 65% boswellic acid;
pumpkin seed oil extract from 100-200 mg per single dose;
from 100-200 mg per single dose turmeric extract containing 65-95% curcuminoids;
green tea EGCG extract, from 30-50 mg per single dose; and,
*Piper nigrum* from 5-10 mg per single dose.

7. The composition according to claim 1, in the form of a liquid or gel, comprising:
D-mannose in an amount from 1500-1700 mg per single dose;
from 300-500 mg per single dose *Boswellia* extract having at least 65% boswellic acid;
pumpkin seed oil extract, from 500-700 mg per single dose;
from 500-700 mg per single dose turmeric extract containing 65-95% curcuminoids;
green tea EGCG extract,
from 90-150 mg per single dose; and,
*Piper nigrum* from 5-20 mg per single dose.

8. The composition according to claim 1, in the form of a powder in a capsule, comprising:
D-mannose 400 mg;
pumpkin seed extract equivalent to 150 mg;
turmeric extract equivalent to 150 mg;
*Boswellia serrata* extract equivalent to 100 mg;
green tea extract 95% polyphenols 30 mg;
black pepper 5 mg; and
optionally, a pharmaceutically acceptable carrier, excipient or diluent.

9. The composition according claim 1, wherein the pumpkin seed extract is from the seeds of one of Cucurbitaceae *maxima*, Cucurbitaceae *pepo* or Cucurbitaceae *moschata*.

10. The composition according to claim 1 suitable for use in combating and reliving the symptoms of a urinary tract infection (UTI).

11. The composition according to claim 1 suitable for use in combating the recurrence of a urinary tract infection.

12. A composition according to claim 1 suitable for use as an antispasmodic for those suffering with overactive bladder syndrome.

13. The composition according to claim 1 suitable for use in combating post-coital and/or sexual-activity triggered UTIs.

14. A composition for use in the treatment of a urinary tract infection, by administering four capsules three times a day for a minimum of 5 days, wherein the capsule comprises:
D-mannose 400 mg,
pumpkin seed extract 10:1, equivalent to 150 mg,
turmeric extract 10:1, equivalent to 150 mg,
*Boswellia serrata* extract 5:1, equivalent to 100 mg,
green tea extract 95% with polyphenols 30 mg,
black pepper 5 mg; and
optionally, a pharmaceutically acceptable carrier, excipient, or diluent.

* * * * *